United States Patent

Banko

[19]

[11] Patent Number: 6,165,150
[45] Date of Patent: Dec. 26, 2000

[54] TIPS FOR ULTRASONIC HANDPIECE

[75] Inventor: William Banko, Mamaroneck, N.Y.

[73] Assignee: Surgical Design Corporation, Long Island City, N.Y.

[21] Appl. No.: 08/998,809

[22] Filed: Dec. 29, 1997

[51] Int. Cl.[7] ............................................ A61B 17/20
[52] U.S. Cl. ............................................ 604/22; 604/902
[58] Field of Search .................... 604/22, 902; 606/167, 606/169, 272

[56] References Cited

U.S. PATENT DOCUMENTS

| | | | |
|---|---|---|---|
| 5,718,676 | 2/1998 | Barrett ........................................ | 604/22 |
| 5,725,495 | 3/1998 | Strukel et al. ............................. | 604/44 |
| 5,788,679 | 8/1998 | Gravlee, Jr. ............................... | 604/272 |
| 5,836,897 | 11/1998 | Sakurai et al. ............................ | 601/2 |
| 5,836,959 | 11/1998 | Seibel et al. .............................. | 606/169 |
| 5,980,529 | 11/1999 | Strukel ...................................... | 606/107 |
| 5,984,904 | 11/1999 | Steen et al. ............................... | 604/264 |
| 5,989,209 | 11/1999 | Barrett ....................................... | 604/22 |
| 5,993,408 | 11/1999 | Zaleski ...................................... | 604/22 |
| 6,007,555 | 12/1999 | Devine ...................................... | 606/169 |
| 6,074,396 | 11/1999 | Geuder ...................................... | 606/107 |

*Primary Examiner*—Wynn Wood Coggins
*Assistant Examiner*—Cris L. Rodriguez

[57] ABSTRACT

An ultrasonic instrument has a generator of ultrasonic energy and an elongated tip whose proximal end receives the ultrasonic energy from the generator which is conveyed to the tip distal end having a distal end section with an outer surface that is non-circular with a part, such as the corner junction between two walls of a polygon, having a shape to concentrate the ultrasonic energy at the tip distal end for radiation outwardly from the tip. One form of tip distal end section has a diamond shaped cross-section that can be either transverse or at an angle to the tip longitudinal axis.

13 Claims, 3 Drawing Sheets

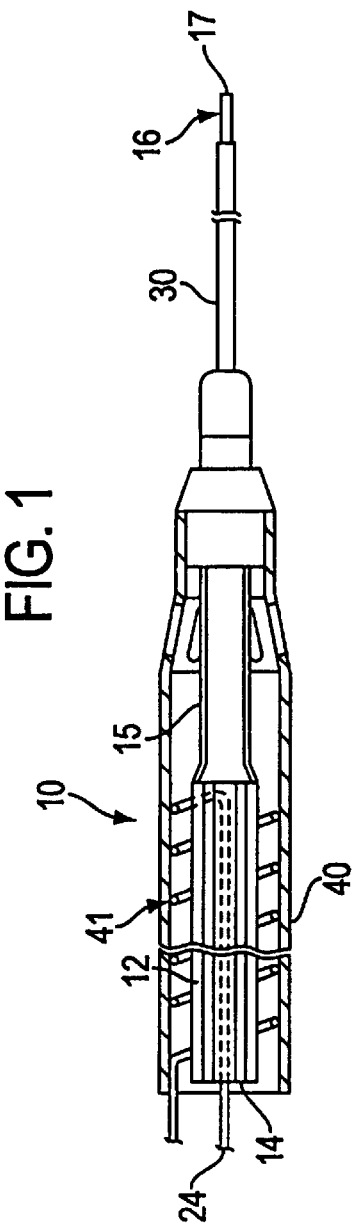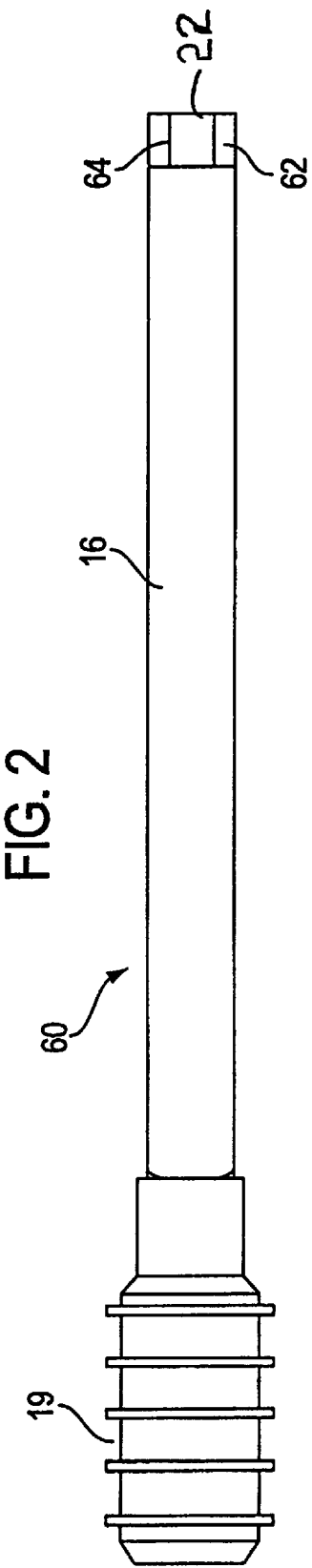

TIPS FOR ULTRASONIC HANDPIECE

RELATED APPLICATION

Reference is made to co-pending U.S. application Ser. No. 08/458,409, filed on Jun. 2, 1995 now abandoned, which is assigned to the same assignee as the subject application. That application, and its divisional counterparts, the disclosures of which are incorporated herein by reference, discloses improvements in ultrasonic surgical instruments, including various types of tips, or needles, to which ultrasonic energy is applied to perform surgical operations. Reference is also made to the co-pending application of Terence M. Devine, Ser. No. 08/845,990 filed Apr. 25, 1997, now U.S. Pat. No. 6,007,555 granted Dec. 28, 1999 filed Apr. 25, 1997 and entitled "Ultrasonic Needle for Surgical Emulsification".

BACKGROUND OF THE INVENTION

Various types of ultrasonic handpieces are utilized for surgical applications, for example, ophthalmic surgery for the removal of cataracts or other tissue. Typically, such handpieces use some type of vibrating transducer, such as of the magnetostrictive or piezoelectric type, which converts electrical energy into mechanical energy. The mechanical energy is used to vibrate a tip, or needle, of the handpiece and the tip distal end emulsifies the tissue with which it comes into contact. The tip is often of a configuration, such as having a hollow interior, to provide a passage for aspiration (evacuation) of the emulsified tissue to a line in the handpiece to be conveyed to a disposal container. The handpiece also often has a line for providing irrigation fluid to the operating site.

It is always an object to improve the overall efficiency of the handpiece and expand its use. A typical ultrasonic handpiece uses a standard tip with an inner aspiration fluid flow passage and has uniform inner and outer diameters along its length. In U.S. Pat. No. 5,242,385, granted on Sep. 7, 1993 to Igor Strukel and assigned to the assignee of the subject application, an improved ultrasonic handpiece and tip are disclosed. The handpiece, which is of the magnetostrictive type, utilizes various improvements in lamination structure to increase the efficiency of the conversion of the electrical to mechanical energy. The patent also discloses a novel tip which is marketed by Surgical Design Corporation of Long Island City New York as the COBRA tip.

The COBRA tip of the aforesaid patent has a distal end section with a circular outer surface that is enlarged relative to the remainder of the tip. The enlarged end section includes the terminal end of the aspiration passage that can be of the same or different diameter from the passage of the remainder of the tip. The exposed end of the tip enlarged distal end section contacts the tissue at the operating site and some of it is drawn into the aspiration passage of the end section by the handpiece evacuation force to be emulsified by the tip vibratory energy. To improve the transfer of the mechanical vibratory energy produced by the handpiece to the tip, the interior of the tip enlarged distal end section preferably is formed of at least two portions of different diameter which are connected by a transition section. This defines at least one interior angle between adjacent ends of the sections of different diameters from which vibratory energy emanates to be more effectively directed, or focused, to effect the tissue emulsification within the aspiration passage. U.S. Pat. No. 5,213,569 to Peter Davis, granted May 25, 1993 discloses a tip whose distal end face end is shaped, by being dished out, to focus the ultrasonic energy at a point exterior of the tip. The outer surface of the tip distal end is circular and the tip end face can be either transverse or at angle to the tip longitudinal axis.

BRIEF DESCRIPTION OF THE INVENTION

The present invention relates to an improvement in the handpiece of the aforesaid U.S. Pat. No. 5,242,385 and particularly to improvements in tips of either the standard configuration having a uniform diameter along its length and in those with an enlarged distal end section, such as in the COBRA tip. It has been found to be useful to modify the normal circular shape of the outer surface of the distal end of such tips to improve the efficiency of certain surgical operating procedures and to permit development of new procedures. In accordance with the invention, the outer diameter of a section of the distal end of the tip is made of a non-circular shape, for example, in the shape of a polygon, such as a triangle, square, rectangle, diamond, pentagon, hexagon, etc. The outer diameter also can be fluted around all, or a part of, its outer diameter. Where the outer diameter is of polygonal shape, the corner junction between adjacent sides of the polygon can be tapered or rounded.

Making the outer surface of the tip distal end noncircular provides the advantage of being able to better focus transmission of the tip ultrasonic energy to a desired part of the tissue. This has certain advantages over prior art types of tips having a circular outer surface. For example, in certain ophthalmic surgical applications, such as in the removal of cataracts, the cataract may contain a hard nucleus. Previously, cracking the nucleus was accomplished by mechanical manipulation of a surgical tool against the nucleus. An improved tip according to the invention permits the nucleus to be cracked by the application of ultrasonic energy. In the case of cracking the nucleus described above, a tip embodying the principles of the invention having a distal end section with the cross-section of a diamond shaped polygon can be used. The tapered transition between two generally flat side walls of the diamond shaped polygon, that is, the corner junction between the two walls, is placed close to or in contact with the nucleus. The ultrasonic energy at the distal end section corner junction is concentrated and focused and transmitted the nucleus. The energy transmitted is sufficient to produce a crack in the nucleus that can then be separated fully by another instrument applying force along the crack.

In a preferred embodiment of the invention, the inner passage of the tip is maintained with a circular configuration. Therefore, the inner and outer diameters of the distal end section are not symmetrical. Also, the end face of the distal end section, that is, the entrance to the aspiration passage, can be either transverse to the tip longitudinal axis or at an angle to the axis.

OBJECTS OF THE INVENTION

It is therefore an object of the present invention to provide an ultrasonic handpiece with an improved tip.

Another object of the invention is to provide improved tips for ultrasonic surgical instruments.

A further object is to provide tips for ultrasonic surgical instruments of both the standard type of uniform outer diameter and of the type with an enlarged distal end portion in which the outer surface of the tip distal end section is noncircular.

An additional object is to provide tips for ultrasonic surgical instruments of both the standard type of uniform outer diameter and of the type with an enlarged distal end section in which the outer surface of the tip distal end section is noncircular.

BRIEF DESCRIPTION OF THE DRAWINGS

Other objects and advantages of the present invention will become more apparent upon reference to the following specification and annexed drawings in which:

FIG. 1 is view illustrating the general structure of one type of conventional ultrasonic handpiece;

FIG. 2 is a plan view of a tip with uniform inner and outer diameters along its length;

DETAILED DESCRIPTION OF THE INVENTION

Figure 3:
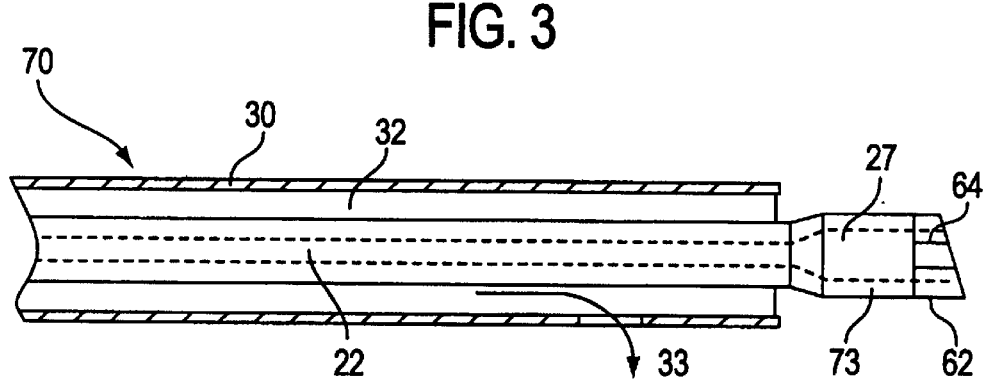
FIG. 3 is a plan view of a tip with an enlarged distal end section.

FIG. 1 shows the basic structure of a surgical instrument handpiece 10 for producing ultrasonic energy and FIGS. 2 and 3 show general forms of tips incorporating the invention that are used with the handpiece 10. The handpiece 10 illustrated is of the magnetostrictive type, but the tips of the invention also have applicability to handpieces using other types of ultrasonic energy producing devices, such as of the piezoelectric type.

In the handpiece 10 of FIG. 1 there is a stack of laminations 12 of a suitable material, for example, nickel, within the handpiece outer housing 40 for converting electromagnetic energy received from an energized coil of wire 41 wound around the stack. The non-working end 14 of the lamination stack is connected together by brazing or welding with a suitable metal material. One end of an acoustic impedance transformer body 15 is connected to the other end of the lamination stack. Acoustic transformer 15 is a body of a metal material of suitable shape and dimensions necessary to convert the vibrations of the lamination stack into vibratory motion along a longitudinal direction.

An elongated work tip, or needle, 16 of a suitable material, such as titanium, is connected to the other end of the acoustic body 15. The tip proximal end receives the longitudinal vibratory energy from acoustic body 15 which is conveyed along the length of the tip to its distal end 17 to perform work. The proximal end of the tip usually is formed with a connecting means 19, such as threads as shown in FIG. 2, or a detent lock, to attach the tip to mating connecting means (not shown) on the acoustic body 15. A handpiece also can be made with a tip that is permanently connected to the acoustic body.

The tip 16 is hollow and has a central passage 22, as shown in FIGS. 2 and 3, along its length. Passage 22 provides a fluid flow path from the tip distal end 17 to a conduit 24 on the handpiece which is connected to an aspiration (evacuation) fluid flow source (not shown). This provides an aspiration, that is, a suction flow, path for the material, such as tissue, emulsified at the tip end 17. A sleeve 30 usually surrounds a portion of the tip length to provide a passage 32 for irrigation fluid to be dispensed through a sleeve port 33 to the operating site. All of this is conventional in the art.

FIG. 2 shows a tip 60 of the standard type, that is, one that has a uniform overall outer diameter along its length. In accordance with the invention, the tip 60 has a section 62 at its extreme distal end with a non-circular outer surface, as indicated by the lines 64. The non-circular outer surface can be any one of the several types described below, such as flat sides to form a polygon. That is, the outer periphery of the cross-section transverse to the tip longitudinal axis is non-circular over the length of the distal end section 62. Typically, for the standard tip 60 the overall outer diameter of the end section 62 measured around the non-circular outer surface, such as over the corners joining the polygon flat sides, is substantially the same as the outer diameter of the more proximal major part of the tip length. The tip 60 inner central aspiration passage 22 is of uniform diameter along its length.

In the manufacture of the tip of FIG. 2, a tubular member of circular outer shape is used and the end section 62 outer surface is machined to obtain the desired shape. Any suitable, conventional machining process can be used including grinding, etching, laser etching, etc. The thickness of the wall of tip 16 along its length may be made slightly greater than that of a conventional tip to provide structural strength for the wall of the machined end section 62. This can be done by any one or combination of reducing the diameter of the central passage 22 or increasing the tip outer diameter.

FIG. 3 shows a tip 70 of the type of the aforesaid U.S. Pat. No. 5,242,385. The tip outer surface is circular along most of its length and has an end portion 73 that is of greater outer diameter than the more proximal major portion of the tip length. Here, the enlarged end portion 73 has a section 62 at the extreme distal end whose outer surface is non-circular, as is shown with the lines 64, to have one of the several shapes described below. The non-circular distal end section 62 can extend along only a portion of the enlarged end portion 73 or can be along its entire length.

In the tip 70, the aspiration passage is shown as circular with two sections of different diameter. The section 27 at the enlarged end portion 73, which is the inlet to the aspiration passage for tissue and liquid from the operating site, is larger than the section 22 of the remaining major length of the tip. The interior of the tip distal end can be made by machining a solid piece with reamers of two different diameters to produce the passage sections 22 and 27. The inner surface of the tip enlarged end portion 73 also can have angled sections and the passage section 27 can be offset from the center line of the passage section 22 to direct the propagation of the ultrasonic energy and/or the aspiration flow. This is described in U.S. Pat. No. 5,242,385 and the aforementioned application Ser. No. 08/458,409. The outer surface of the end portion 73 is machined to achieve the desired shape for the distal end section 62 non-circular outer surface. In this type of tip, the wall thickness of the enlarged end portion 73 can be made thicker than normal and then machined down to the desired outer surface shape for section 62.

FIGS. 4–11 are end views of a variety of distal end sections 62 of either of the tip types 60 and 70 of FIGS. 2 and 3. That is, any of the non-circular distal end sections 62 can be used with either of the types of tips shown in FIGS. 2 and 3. The same reference numbers are used for the same elements throughout the description. All of the tip end views are shown with the top of the tip end face, that is the face with the entrance to the aspiration passage, at the top of the figure and the top of the handpiece 10 used in its normal operating condition relative to the tip, as shown in FIG. 1. Other fixed alignments of the tip relative to the handpiece are possible and the user of the instrument can rotate and angulate the handpiece during its use to achieve any desired orientation of the tip distal end section 62 relative to the operating site.

Figure 4:
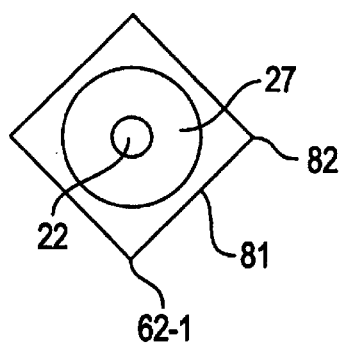
FIGS. 4–11 are views of other shapes of tip distal end sections in accordance with the invention.

FIG. 4 shows a preferred embodiment of the invention having an end section 62-1 that is of diamond shaped cross-section. That is, the end section outer surface is formed with four flat sides 81 of equal length and an angular corner junction 82. Also, one corner junction 82 of two adjacent sides is aligned with the center of the top of the handpiece 10 as it is being used. The end section 62-1 is illustrated for a tip 70 with an enlarged end porion 73, as in FIG. 3, and circular aspiration passage portions 22 and 27 of different diameters are shown.

Figure 4A:
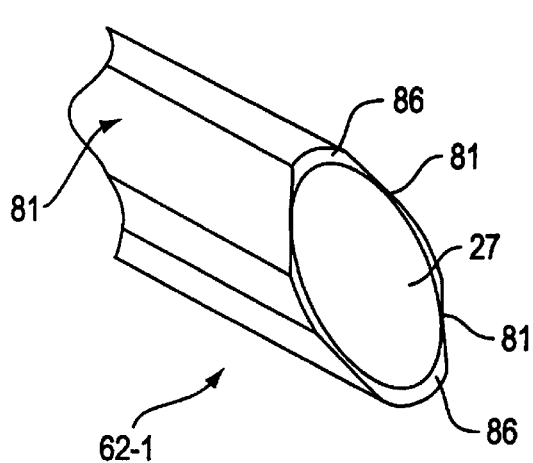

The terminating distal end face of the section 62, that is, the entrance to the aspiration passage, can be transverse to the tip longitudinal axis, as shown in FIG. 2, or, as shown in FIG. 4A, can be at an angle relative to the tip longitudinal axis. In addition, in FIG. 4A instead of the 90° angular corner 82 joining the two adjacent walls 81, there is a rounded corner 86. The corner 86 can be formed by not flat machining the entire outer surface of the end section 62.

When the diamond shaped tip end section 62-1 is used for a standard type tip 60, then there would only be the circular aspiration passage 22 of one uniform diameter. Whether the tip is of the standard type as shown in FIG. 2 or the enlarged end portion type as shown in FIG. 3, there is only one entrance port for the aspiration flow passage at the terminating end face of the tip. This is hereafter designated with reference number 27 for both types of tips.

In a tip with a circular distal end outer surface, the energy is radiated substantially uniformly from around the entire tip surface. In the diamond shaped cross-sections of the tips of FIGS. 4 and 4A, the ultrasonic energy tends to be concentrated at the corners 82 and 86. The user of the instrument would position a corner of the tip at a point of the operating site, such as the nucleus of the cataract, where application of a concentration of the ultrasonic energy is desired. This desired result can be achieved without increasing the overall amount of energy produced by the tip which might be radiated to undesired places. The diamond shaped end section is also advantageous since it permits the user of the handpiece to position a tip corner 82 or 86 at the desired point of the operating site while still maintaining the handpiece in its normal operating position.

Figure 5:
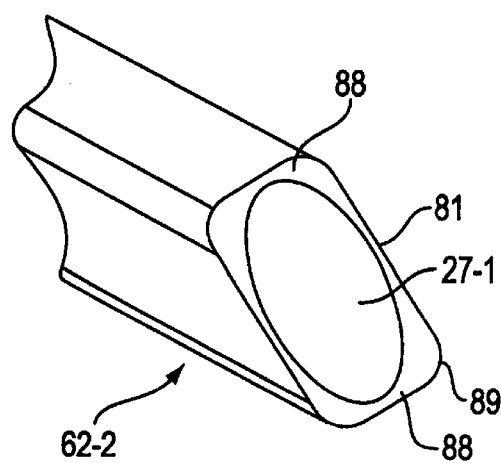

FIG. 5 shows a rectangular shaped end section 62-2 with flat side walls 81 and end walls 88 joined by rounded corners 89. The distal end face is at an angle relative to the tip longitudinal axis so the circular passage at the tip distal end appears oval and is represented by the number 27-1.

Figure 6:
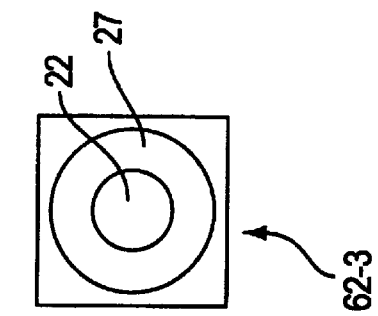

FIG. 6 is an end view of another tip end section 62-3 of square cross-section in which the end face is transverse to the tip longitudinal axis. Here, the passage 27 is circular. FIG. 6 would be an end view of tip end section 62-2 of FIG. 5 if the end face of FIG. 5 was square and not rectangular and with the corners rounded. If the tip of FIG. 6 is rotated by 45 relative to the top of the instrument, then the diamond shape end face of FIG. 4 is obtained.

Figure 8:
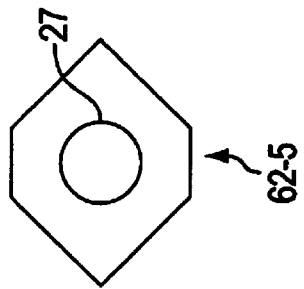
Figure 7:
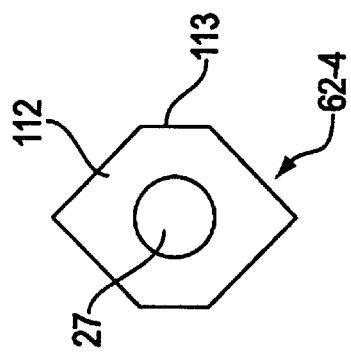
Figure 10:
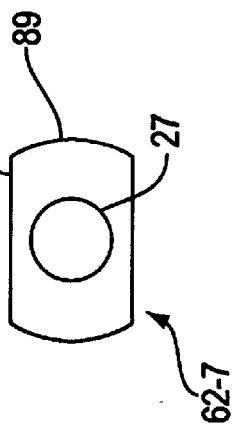
Figure 9:
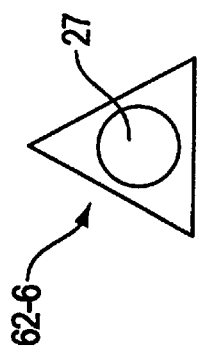

The tip distal end sections 62 of FIGS. 4–6 have overall cross-sections of four sided regular and modified polygons with a circular exit for passage 27. Other polygonal cross-sections are also possible. In FIG. 7, there is a hexagonal distal end section 62-4 of irregular shape with the angular sides 112 being longer in the vertical direction than the vertical sides 113. FIG. 8 shows an end section 62-5 of regular hexagonal shape. FIG. 9 shows an end section 62-6 of triangular cross-section. Also, as in the case of the tip cross-sections previously described, the end face can be either transverse or at an angle to the tip longitudinal axis. The corners joining the walls can be rounded or chamfered in any of the end sections 62. Other polygonal shapes can be used. FIG. 10 shows a tip end section 62-7 with opposing flat walls 81 joined by rounded wall sections 89.

In each of the end sections of FIGS. 4-10 the cross-section of the distal end section has two adjacent flat walls with a corner junction that can be either angular, rounded, tapered or bevelled. The ultrasonic energy is concentrated at and radiated outwardly of the tip from the corner junction.

Figure 11:
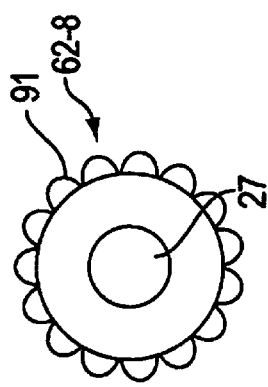

In FIG. 11 the end section 62-8 has flutes 91. Here also, the aspiration passage 27 is circular. The ultrasonic energy is concentrated at the high points of the flutes.

Each of the tips of FIGS. 4–11 is shown with a circular aspiration passage 22, 27 along its entire length. This has an advantage from the point of view of ease of tip manufacture. It is also possible to make the aspiration passage, at least at the distal end part 27, to have the same shape as the distal end section outer surface. For example, if the end section 62 cross-section is triangular, then the passage part 27 will be triangular. This also applies to the other tip end section cross-sections.

While the present invention has been particularly shown and described with respect to certain preferred and illustrative embodiments, it will be understood by those skilled in the art that variations and modifications may be made therein without departing from the spirit and scope of the present invention which is limited only by the attached claims.

I claim:

1. A tip for an ultrasonic instrument including a generator of ultrasonic energy, said tip being elongated and having a proximal end which receives the ultrasonic energy from the generator and a distal end to which the energy is conveyed; and said tip having a section at its extreme distal end with an outer surface having a shape comprising two flat walls forming a corner junction of substantially 90° or less to concentrate the ultrasonic energy at the tip distal end for radiation outwardly from the tip and a central passage along the tip length with the surface forming said central passage in said distal end section being continuous thereround.

2. A tip for an ultrasonic instrument as in claim 1 wherein the outer surface of said tip is circular along its length up to said distal end section.

3. A tip for an ultrasonic instrument as in claim 1 wherein said distal end section is one of substantially the same overall outer size as the portion of the tip length proximal of said distal end section or that is of greater outer size than said portion proximal of said distal end section.

4. A tip for an ultrasonic instrument as in claim 1 wherein the outside of said corner junction between said two walls is one of angular, rounded, tapered or beveled shape.

5. A tip for an ultrasonic instrument as in claim 1 wherein the cross-section of said distal end section is a polygon with at least three walls, there being a said corner junction between any two adjacent walls.

6. A tip for an ultrasonic instrument as in claim 5 having a face at the extreme distal end of said distal end section that is one of transverse to the tip longitudinal axis or at an angle to said longitudinal axis.

7. A tip for an ultrasonic instrument as in claim 5 wherein a said corner junction is one of angular, rounded, tapered or beveled shape.

8. A tip for an ultrasonic instrument as in claim 1 wherein said distal end section has a cross-section of a diamond shape formed by four connected walls with a corner junction between two adjacent walls.

9. A tip for an ultrasonic instrument as in claim 8 having a face at the extreme distal end of said distal end section that is one of transverse to the tip longitudinal axis or at an angle to said longitudinal axis.

10. A tip for an ultrasonic instrument as in claim 9 wherein said distal end section is one of substantially the same overall outer size as the portion of the tip length proximal of said distal end section or that is of greater outer size than said portion proximal of said distal end section.

11. A tip for an ultrasonic instrument as in claim 9 wherein a said corner junction is one of angular, rounded, tapered or beveled shape.

12. A tip for an ultrasonic instrument as in claim 1 wherein said outer surface of said distal end section has a plurality of flutes therearound.

13. A tip for an ultrasonic instrument as in claim 1 wherein said central passage is generally circular along its length.

\* \* \* \* \*